US010898611B2

(12) United States Patent
Williams et al.

(10) Patent No.: US 10,898,611 B2
(45) Date of Patent: Jan. 26, 2021

(54) CANCELLOUS BONE PRODUCT INCLUDING VIABLE OSTEOGENIC CELLS

(71) Applicant: NuVasive, Inc., San Diego, CA (US)

(72) Inventors: Michelle LeRoux Williams, Laurel, MD (US); Charles Randal Mills, Finksburg, MD (US); Rodney Monroy, Aberdeen, MD (US); Robert A. Zambon, Rockville, MD (US); Dayna Buskirk, Gainesville, FL (US); Earl Fender, Plano, TX (US)

(73) Assignee: NuVasive, Inc., San Diego, CA (US)

( * ) Notice: Subject to any disclaimer, the term of this patent is extended or adjusted under 35 U.S.C. 154(b) by 303 days.

(21) Appl. No.: 15/622,985

(22) Filed: Jun. 14, 2017

(65) Prior Publication Data

US 2017/0281348 A1 Oct. 5, 2017

Related U.S. Application Data

(63) Continuation of application No. 12/150,513, filed on Apr. 28, 2008, now abandoned, which is a continuation-in-part of application No. 11/799,606, filed on May 2, 2007, now Pat. No. 8,460,860.

(60) Provisional application No. 60/831,723, filed on Jul. 18, 2006, provisional application No. 60/798,474, filed on May 8, 2006.

(51) Int. Cl.
*A61L 27/36* (2006.01)
*A61F 2/28* (2006.01)

(52) U.S. Cl.
CPC ......... *A61L 27/365* (2013.01); *A61L 27/3608* (2013.01); *A61L 27/3687* (2013.01); *A61F 2/28* (2013.01); *A61F 2310/00359* (2013.01)

(58) Field of Classification Search
CPC .................................................... A61L 27/365
See application file for complete search history.

(56) References Cited

U.S. PATENT DOCUMENTS

| | | |
|---|---|---|
| 4,065,816 A | 1/1978 | Sawyer |
| 4,108,161 A | 8/1978 | Samuels et al. |
| 4,802,853 A | 2/1989 | Krasner |
| 5,118,512 A * | 6/1992 | O'Leary ............... A01N 1/0221 424/520 |
| 5,345,746 A | 9/1994 | Franchi |
| 5,385,229 A | 1/1995 | Bittmann et al. |
| 5,480,424 A | 1/1996 | Cox |
| 5,531,791 A | 7/1996 | Wolfinbarger, Jr. |
| 5,676,146 A | 10/1997 | Scarborough |
| 5,697,383 A | 12/1997 | Manders et al. |
| 5,788,941 A * | 8/1998 | Dalmasso ............ A61L 2/0094 422/33 |
| 5,901,315 A | 5/1999 | Edwards |
| 5,910,315 A * | 6/1999 | Stevenson ............ A61F 2/4601 424/422 |
| 5,989,498 A | 11/1999 | Odland |
| 6,024,735 A | 2/2000 | Wolfinbarger, Jr. |
| 6,083,690 A | 7/2000 | Harris et al. |
| 6,189,537 B1 | 2/2001 | Wolfinbarger, Jr. |
| 6,203,755 B1 | 3/2001 | Odland |
| 6,254,635 B1 | 7/2001 | Schroeder et al. |
| 6,293,970 B1 | 9/2001 | Wolfinbarger, Jr. |
| 6,294,187 B1 | 9/2001 | Boyce |
| 6,311,690 B1 | 11/2001 | Jefferies |
| 6,432,436 B1 | 8/2002 | Gertzman et al. |
| 6,652,818 B1 | 11/2003 | Mills et al. |
| 6,652,872 B2 | 11/2003 | Nevo et al. |
| 6,739,112 B1 | 5/2004 | Marino |
| 7,162,850 B2 | 1/2007 | Marino |
| 2001/0039458 A1 | 11/2001 | Boyer, II et al. |
| 2002/0018796 A1 | 2/2002 | Wironen |
| 2004/0230309 A1 | 11/2004 | DiMauro et al. |
| 2006/0083769 A1 | 4/2006 | Kumar et al. |
| 2006/0240064 A9 | 10/2006 | Hunter et al. |
| 2007/0260326 A1 | 11/2007 | Williams et al. |
| 2008/0262633 A1 | 10/2008 | Williams et al. |

FOREIGN PATENT DOCUMENTS

| | | | |
|---|---|---|---|
| WO | WO0232474 | 4/2002 | |
| WO | WO-0232474 A1 * | 4/2002 | ............. A61K 35/32 |
| WO | WO2007/133451 | 11/2007 | |
| WO | WO2009/134815 | 11/2009 | |

OTHER PUBLICATIONS

Mayer, Hubert. Cells Tissues Organs; Basel vol. 177, Iss. 2: 57-67. (Year: 2004).*
Lambrect et al. Clin Anat 9(1):41-5. (Year: 1996).*
Alberts et al., Chapter 23 Specialized Tissues, Stem Cells and Tissue Renewal, Molecular Biology of the Cell, 5th Edition, 2008, p. 1457, Garland Science, New York, New York.
Caplan, A., "What's in a Name?", Tissue Engineering, 2010, 16(8):2415-2417.
Lambrecht and Marks, "Human Osteoclast-like Cells in Primary Cultures" Clinical Anatomy, 1996, 9:41-45.
Robey et al., "Human Bone Cells In Vitro", Calcif Tissue Int, 1985, 37:453-460.
Sakaguchi et al., "Suspended cells from trabecular bone by collagenase digestion become virtually identical to mesenchymal stem cells obtained from marrow aspirates", Blood, 2004, 104(9):2728-2735.
International Search Report in International Application No. PCT/US07/10589 dated Oct. 24, 2007, 1 page.

(Continued)

*Primary Examiner* — Amy L Clark

(57) ABSTRACT

A bone implant comprising cancellous bone that is essentially free of blood cells, and which has been treated with at least one loosening agent, such as collagenase or a digestive enzyme, for a time and at a concentration to loosen the osteogenic cells in the cancellous bone matrix. The osteogenic cells in the matrix are viable cells. The treatment of the cancellous bone with at least one loosening agent enables the osteogenic cells to be more available for carrying out their osteogenic function and to provide for an increased rate of bone formation. Such implant also may include demineralized bone, such as demineralized cortical bone, which enhances the bone regenerative capacity of the cancellous bone.

22 Claims, No Drawings

(56) References Cited

OTHER PUBLICATIONS

Written Opinion of the International Searching Authority in International Application No. PCT/US07/10589 dated Oct. 24, 2007, 3 pages.
International Search Report in International Application No. PCT/US2009/041999 dated Jun. 24, 2009, 2 pages.
Written Opinion of the International Searching Authority in International Application No. PCT/US2009/041999 dated Jun. 24, 2009, 5 pages.
Cook. In vivo evaluation of DBM as Bone Graft Substitute in Posterior Spinal Fusion. Spine. 1995, 20(8), pp. 877-886.
Gazdag, Alternatives to Autogenous Bone Graft, JAAOS, 1995, 3(1).
An, Comparison Betwen Allograft Plus Demineralized Bone Matrix Versus Autograft in Anterior Cervical Fusion, Spine, 1995, 20(20), pp. 2211-2216.
Osteoclasts and Remodeling Based Bone Formation, Current Stem Cell Research & Therapy, 11:8,2016.

\* cited by examiner

CANCELLOUS BONE PRODUCT INCLUDING VIABLE OSTEOGENIC CELLS

This application is a continuation of pending application Ser. No. 12/150,513 filed Apr. 28, 2008, which was a continuation-in part of application Ser. No. 11/799,606, filed May 2, 2007 which claimed priority based on provisional application Ser. No. 60/831,723, filed Jul. 18, 2006, and provisional application Ser. No. 60/798,474, filed May 8, 2006, the contents of which are incorporated herein by reference in their entireties.

BACKGROUND OF THE INVENTION

This invention relates to bone implants comprising cancellous bone useful in the treatment or prevention of bone diseases, disorders, defects, or injuries.

BRIEF SUMMARY OF THE INVENTION

This invention relates to bone implants which include cancellous bone. More particularly, this invention relates to bone implants that include cancellous bone that has been treated with at least one loosening agent in order to loosen osteogenic cells in the bone matrix. The cancellous bone also is essentially free of blood cells.

This invention also relates to bone implants which include the cancellous bone hereinabove described, and demineralized bone. More particularly, this invention also relates to bone implants which include the cancellous bone hereinabove described, and bone, such as, for example, cortical bone, which has been treated with at least one demineralization agent for a time and at a concentration to expose osteoinductive proteins in the bone matrix.

Bone implants which include cancellous bone have been used in a variety of procedures and treatments, including bone fusions such as spine fusions, disc augmentations in the spine, and bone fill applications employed in the treatments of diseases, disorders, or injuries including, but not limited to, avascular osteonecrosis, osteosarcoma, acute fractures and fracture non-unions, as well as for bone regeneration for orthopedic implants. Such bone in general may be harvested from any source of cancellous bone, including vertebrae, the iliac crest, femur, tibia, or ribs.

Cancellous bone implants in general have included, in addition to osteocytes and osteogenic cells, blood cells including hematopoietic cells. In some implants, the implants have been treated in order to preserve the viability of all the cells in the implant, while in other implants, the viability of the bone cells, including the osteogenic cells, has been destroyed.

The present invention provides a bone implant which includes cancellous bone including viable osteogenic cells which are made more available for carrying out their osteogenic function.

In accordance with an aspect of the present invention, there is provided a bone implant comprising cancellous bone. The cancellous bone is essentially free of blood cells, and has been treated with at least one loosening agent for a time and at a concentration to loosen the osteogenic cells in the cancellous bone matrix. The osteogenic cells in the bone matrix are viable cells.

The term "loosening agent" as used herein, means an agent which may be contacted with a bone matrix for a time and at a concentration sufficient to loosen osteogenic cells in the cancellous bone matrix without releasing the osteogenic cells from the cancellous bone matrix. An exemplary loosening agent useful in accordance with the present invention comprises collagenase. Another exemplary loosening agent useful in accordance with the present invention comprises a digestive enzyme. In some embodiments, the digestive enzyme is selected from the group consisting of trypsin, amylase, lipase, and combinations thereof. In some embodiments, the digestive enzyme is trypsin. In some embodiments, the digestive enzyme is amylase. In some embodiments, the digestive enzyme is lipase. Another exemplary loosening agent useful in accordance with the present invention comprises a combination of collagenase and a digestive enzyme. For a time and at a concentration to loosen the osteogenic cells contained in the bone matrix, but not release the osteogenic cells from the bone matrix.

The term "osteogenic cell", as used herein, means any type of cell having osteoprogenitor potential, that is, any type of cell that is capable of differentiating into a bone cell.

The term "D90", as used herein, refers to the size of the 90th percentile (by number) particle in a cumulative size distribution of all particles sampled.

Although the scope of the present invention is not to be limited to any theoretical reasoning, when the bone implant is essentially free of blood cells and has been treated with a loosening agent in order to loosen the osteogenic cells in the cancellous bone matrix, such osteogenic cells become more available for or are more disposed toward carrying out their osteogenic function, and provide for an increased rate of bone formation. Thus, such bone implants are capable of generating or "growing" bone directly and provide for improved implants vis-a-vis prior art implants, including previously produced cancellous bone implants, and ceramic implants.

DETAILED DESCRIPTION OF THE INVENTION

The compositions of the present invention are useful in the treatment or prevention of bone diseases, disorders, defects, or injuries.

In one embodiment, the present invention comprises a bone implant that comprises: cancellous bone matrix, said cancellous bone matrix being essentially free of blood cells, said cancellous bone matrix having been treated with at least one loosening agent for a time and at a concentration to loosen osteogenic cells in the cancellous bone matrix, said osteogenic cells in the cancellous bone matrix being viable cells.

In one embodiment, the present invention comprises a bone implant that comprises: (i) cancellous bone matrix, said cancellous bone including cancellous bone which is essentially free of blood cells and having been treated with at least one loosening agent for a time and at a concentration to loosen osteogenic cells in the cancellous bone matrix, said osteogenic cells in the cancellous bone matrix being viable cells; and (ii) cortical bone matrix which has been treated with at least one demineralization agent for a time and at a concentration to expose osteoinductive proteins present in the cortical bone matrix.

In some embodiments, the at least one demineralization agent is hydrochloric acid.

The cancellous bone is treated with the loosening agent to loosen the osteogenic cells in the cancellous bone matrix. In one embodiment, the cancellous bone is treated with at least one loosening agent at a concentration of from about 0.1 mg/ml to about 3.0 mg/ml, and in another embodiment from about 1.0 mg/ml to about 3.0 mg/ml. The cancellous bone is treated with at least one loosening agent for a period of time to loosen the osteogenic cells in the cancellous bone matrix, but not release the osteogenic cells from the cancellous bone matrix. In one embodiment, the cancellous bone is treated with at least one loosening agent for about 5 min. to about 3 hrs. In another embodiment, the cancellous bone is treated with at least one loosening agent for about 5 min. to about 30 min. In yet another embodiment, the cancellous bone is treated with at least one loosening agent at a concentration of about 1 mg/ml for about 10 minutes.

Although Applicants do not intend to be limited to any theoretical reasoning, it is believed that, by treating the bone with at least one loosening agent as hereinabove described, such treatment provides for a partial, but not complete, digestion of the components of the bone matrix (such as collagen, for example). Such partial digestion of the components of the bone matrix, loosens, but does not release, osteogenic cells from the matrix, thereby making such cells, as noted hereinabove, more available for or more disposed toward carrying out their osteogenic function.

In general, the cancellous bone is harvested from any cancellous bone bearing source. Such sources include, but are not limited to, vertebral bodies in the spine, the iliac crest, femur, tibia, and ribs. The cortical shell of the bone is removed, and then the bone is cut or milled into desired pieces or shapes. For example, the bone may be cut or milled into bone chips, or may be cut into wedges or plugs, or may be formed into pellets.

The bone then is washed to remove blood cells, such as red blood cells and hematopoietic cells. After the bone is washed, the bone is treated with at least one loosening agent, such as collagenase or a digestive enzyme. As noted hereinabove, the bone is treated with a loosening agent for a time and at a concentration to loosen the osteogenic cells contained in the bone matrix, but not release the osteogenic cells from the bone matrix. In one embodiment, the bone is treated with the loosening agent at a concentration of about 0.1 mg/ml to about 3 mg/ml, and in another embodiment from about 1.0 mg/ml to about 3.0 mg/ml. In another embodiment, the bone is treated for about 5 min. to about 3 hrs. In another embodiment, the bone is treated for about 5 min. to about 30 min. In yet another embodiment, the bone is treated with the loosening agent at a concentration of about 1.0 mg/ml for about 10 minutes.

In one embodiment, subsequent to the treatment with the loosening agent the bone is treated with one or more antibiotics or one or more antimycotics in order to reduce the level of bioburden within the bone. Antibiotics which may be employed include, but are not limited to, gentamicin; vancomycin; penicillins; macrolide antibiotics, such as erythromycin; sulfa-based antibiotics, and combinations thereof. Antimycotics which may be employed include, but are not limited to, amphotericin, fluconazole, and combinations thereof.

After antibiotic or antimycotic treatment, when chipped or milled bone is employed, the chipped or milled bone, if desired, may be filtered through sieves in order to retain pieces of the bone which have a desired size.

After the bone has been washed, treated with the loosening agent and treated with an antibiotic or antimycotic, the bone then may be added to an appropriate preservation medium, such as a cryopreservation or vitrification medium, in which the bone may be preserved and stored, and the osteogenic cells contained therein will remain viable. In one embodiment, the preservation medium may include one or more of glycerol, dimethylsulfoxide, and DMSO. In one embodiment, the preservation medium enables the treated bone to be frozen at temperatures as low as about $-140°$ C. and as high as about $-20°$ C. while maintaining the viability of the osteogenic cells. The present invention also contemplates that the cancellous bone treated with a loosening agent may be combined with bone that has not been treated with a loosening agent prior to packaging as a final product. For example, the cancellous bone treated with the loosening agent may be mixed with bone that has not been treated with a loosening agent, such as allograft bone chips, fragments or powder, or nucleus pulposus. For example, in one embodiment, the bone treated with the loosening agent is admixed with demineralized bone prior to formulation into a final product. In another embodiment, the final product includes about 50 vol. % treated bone, and about 50 vol. % untreated bone.

The bone implant treated with the loosening agent may be administered to an animal in an amount effective to treat a bone disease, disorder, defect, or injury in the animal. The animal may be a mammal, including human and non-human primates. In one embodiment, the animal is a human.

Bone diseases, disorders, defects, or injuries which may be treated by the bone implant treated with the loosening agent include, but are not limited to, degenerative disc disease, avascular osteonecrosis, osteosarcoma fractures, and fracture non-unions. The bone implant treated with the loosening agent also may be employed in bone fusions, such as spine fusions, as well as in disc augmentation, and for bone regeneration in orthopedic implants.

The bone implant treated with the loosening agent may be administered directly to the site of the bone disease, disorder, defect, or injury. Depending upon the form and shape of the implant, the implant may be injected directly into the site affected by the bone disease, disorder, defect, or injury, or the implant may be packed directly into the site affected by the bone disease, disorder, defect, or injury. The implant has a sufficient consistency' such that the implant will be retained at the implantation site long enough for initial bone formation, osteoinductive signaling, and host cell attachment to occur. The present invention also contemplates that the bone implant may be employed in conjunction with devices employed in the treatment of bone diseases, defects, disorders, and injuries, such as, for example, orthopedic cage devices, ceramics, or plates which may be employed in the spine or in bones to promote bone growth and fusion. Furthermore, the bone implant may be used in conjunction with an autologous bone graft. The bone implant also may be administered with antibiotics, such as those hereinabove described, antimycotics, or anti-inflammatory agents. In another embodiment, the bone implant may be administered in combination with osteoinductive factors such as, for example, bone morphogenic proteins, or BMPs, such as BMP-2 and BMP-7, and platelet-derived growth factor (PDGF), which enhance the osteogenic potential of the bone implant. It is to be understood, however, that the scope of the present invention is not intended to be limited to the treatment of any particular bone disease, defect, disorder, or injury, or to any particular form or any particular method of administration of the bone implant.

As noted hereinabove, the cancellous bone may be admixed with demineralized bone. Thus, in accordance with another aspect of the present invention, there is provided a bone implant comprising (i) cancellous bone, said cancellous bone including cancellous bone which is essentially free of blood cells, as hereinabove described, which has been treated with at least one loosening agent for a time and at a concentration to loosen the osteogenic cells in the cancellous bone matrix, wherein the osteogenic cells in the bone matrix are viable cells; and (ii) bone which has been treated with at least one demineralization agent for a time and at a concentration to expose osteoinductive proteins present in the bone matrix.

In another embodiment, the cancellous bone, in addition to the treated cancellous bone hereinabove described, further comprises bone that has not been treated with a loosening agent.

Although the scope of the present invention is not to be limited to any theoretical reasoning, Applicants have discovered that the demineralized bone enhances the bone regenerative capacity of the cancellous bone.

In one embodiment, the bone which is treated with the at least one demineralization agent is cortical bone.

In one embodiment, the at least one demineralization agent which is used to treat the bone, such as, for example, cortical bone, includes, but is not limited to, any acidic solution. In another embodiment, the at least one demineralization agent is hydrochloric acid.

The bone, such as, for example, cortical bone, is treated with the at least one demineralization agent for a time and at a concentration to expose osteoinductive proteins present in the bone matrix. Such osteoinductive proteins include, but are not limited to, a heterogeneous mixture of bone morphogenic proteins and growth factors. In one embodiment, the bone, such as, for example, cortical bone, is treated with the at least one demineralization agent, such as hydrochloric acid, at a concentration of from about 0.1N to about 12N. In another embodiment, the bone, such as, for example, cortical bone, is treated with the at least one demineralization agent, such as hydrochloric acid at a concentration, for example, of about 0.5N.

In one embodiment, the bone, such as, for example, cortical bone, is treated with the at least one demineralization agent for a period of time of from about 1 minute to about 72 hours. In another embodiment, the bone, such as, for example, cortical bone, is treated with the at least one demineralization agent for a period of time of from about 15 minutes to 180 minutes. In another embodiment, the bone, such as, for example, cortical bone, is treated with the at least one demineralization apart for a period from about 30 minutes to about 120 minutes. In another embodiment, the bone, such as, for example, cortical bone, is treated with the at least one demineralization agent for a period of time of from about 50 minutes to 70 minutes.

In one embodiment, the bone, such as, for example, cortical bone, comprises particles which have a $D_{90}$ of less than about 1,500 microns. In another embodiment, the particles have a $D_{90}$ of about 125 microns to about 1,500 microns. In yet another embodiment, the particles have a $D_{90}$ of about 780 microns to about 1,500 microns. In another embodiment, the particles have a $D_{90}$ of about 125 microns to about 780 microns. In another embodiment, the particles have a $D_{90}$ of about 600 microns to about 900 microns. In another embodiment, the particles have a $D_{90}$ of about 700 microns to about 800 microns. In another embodiment, the particles have a $D_{90}$ of about 780 microns.

In still another embodiment, the bone, such as, for example, cortical bone, comprises a first portion comprising particles having a $D_{90}$ from about 780 microns to about 1,500 microns, and a second portion comprising particles having a $D_{90}$ from about 125 microns to about 780 microns.

In general, the bone, such as, for example, cortical bone, is harvested from any bone bearing source. Such sources include, but are not limited to, the iliac crest, femur, humerus, tibia, fibula, radius, ulna, and ribs. The bone, such as, for example, cortical bone, is removed from its source, and then is cut or milled into particles. The particles then may be separated according to size, such as by passing the particles through one or more sieves. For example, the particles may be passed through a 1,500 micron sieve, then through a 780 micron sieve, and then through a 125 micron sieve. Such sieving provides a portion of bone particles having a $D_{90}$ from 780 microns to 1,500 microns, and another portion of bone particles having a $D_{90}$ from 125 microns to 780 microns.

The sieved bone then is treated with at least one demineralization agent for a time and at a concentration to expose osteogenic proteins present in the cortical bone matrix. In one embodiment, the bone particles, such as, for example, cortical bone particles, are treated with hydrochloric acid at a concentration of about 0.5N for a period of time of from about 15 minutes to 180 minutes. In one embodiment, the bone particles, such as, for example, cortical bone particles, are treated with hydrochloric acid at a concentration of about 0.5N for a period of time of from about 30 minutes to 120 minutes. In one embodiment, the bone particles, such as, for example, cortical bone particles, are treated with hydrochloric acid at a concentration of about 0.5N for a period of time of from about 50 minutes to 70 minutes.

In one embodiment, subsequent to the treatment with the at least one demineralization agent, the bone, such as, for example, cortical bone is treated with one or more antibiotics or one or more antimycotics in order to reduce the level of bioburden within the bone. Antibiotics and antimycotics which may be employed include, but are not limited to, those mentioned hereinabove with respect to treatment of the cancellous bone.

After the bone, such as, for example, cortical bone, has been treated as hereinabove described, it then is combined with the cancellous bone to provide a bone implant product.

In one embodiment, the bone implant includes at least about 50 vol. % of the cancellous bone hereinabove described, and up to about 50 vol. % of the demineralized bone, such as demineralized cortical bone, as hereinabove described. In another embodiment, the bone implant includes from about 55 vol. % to about 85 vol. % of the cancellous bone, and from about 15 vol. % to about 45 vol. % of the demineralized bone. In yet another embodiment, the bone implant includes from about 55 vol. % to about 65 vol. % of the cancellous bone, and from about 35 vol. % to about 45 vol. % of the demineralized bone.

In one embodiment, the bone implant includes at least about 50 vol. % of the cancellous bone hereinabove described, from about 5 vol. % to about 40 vol. % of demineralized bone particles, such as demineralized cortical bone particles, having a $D_{90}$ from about 780 microns to about 1,500 microns, and from about 5 vol. % to about 20 vol. % of demineralized bone particles, such as demineralized cortical bone particles, having a $D_{90}$ from about 125 microns to about 780 microns.

In one embodiment, the cancellous bone is present in the bone implant in an amount of from about 55 vol. % to about 85 vol. %. In another embodiment, the cancellous bone is present in the bone implant in an amount of from about 55 vol. % to about 65 vol. %. In still another embodiment the cancellous bone is present in the bone implant in an amount of from about 57 vol. % to about 65 vol. %.

In one embodiment, the demineralized bone particles, such as demineralized cortical bone particles, having a $D_{90}$ from about 780 microns to about 1,500 microns are present in the bone implant in an amount of from about 5 vol. % to about 30 vol. %. In another embodiment, the demineralized bone particles having a $D_{90}$ from about 780 microns to about 1,500 microns are present in the bone implant in an amount of from about 24 vol. % to about 28 vol. %.

In one embodiment, the demineralized bone particles, such as demineralized cortical bone particles, having a $D_{90}$ from about 125 microns to about 780 microns are present in the bone implant in an amount of from about 8 vol. % to about 18 vol. %. In yet another embodiment, the demineralized bone particles having a $D_{90}$ from about 125 microns to about 780 microns are present in the bone implant in an amount of about 18 vol. %.

The bone implant including the cancellous bone and demineralized bone, such as, for example, demineralized cortical bone, may be added to an appropriate preservation medium, such as a cryopreservation medium or vitrification medium as hereinabove described, in which the bone implant may be stored prior to use.

Such bone implant, which includes the cancellous bone and demineralized bone as hereinabove described, may be used to treat the bone defects, disorders, and injuries hereinabove described, and may be administered directly to the site of the bone disease disorder, defect, or injury as hereinabove described to treat such disease, disorder, defect, or injury.

The invention now will be described with respect to the following examples. It is to be understood, however, that the scope of the present invention is not intended to be limited thereby.

Example 1

A bone sample was removed from a saline holding solution after debridement of soft tissue, and swabbed with a wiper. The bone was placed in a cutting area, and positioned face up. The bone then was cut with a reciprocating saw to remove the cortical shell. The remaining bone then was placed into a 500 ml washing bag filled halfway with saline (0.9%) and anticoagulant citrate dextrose solution, Formula A (ACD-A), at a ratio of 9 parts 0.9% saline to one part ACD-A. The bag lid then was closed, and shaken vigorously. The bone sample then was retrieved from the washing solution, and then placed into a bone milling chamber. The bone was then milled, and then the milled bone was spooned out, and placed into a 500 ml receiver bottle containing up to 300 ml of 0.9% saline and ACD-A at a volume ratio of 9 parts saline to one part ACD-A.

The milled bone then was washed. First, the wash solution was decanted from the receiving bottle into a waste beaker. The wash solution was replaced with a new wash solution of 0.9% saline and ACD-A (volume ratio of 9 parts saline to one part ACD-A), the lid on the receiver bottle was tightened, and the bottle was shaken vigorously. The above washing was repeated until the wash solution was clear, and the chips of milled bone were white to off-white in color. The last wash solution was decanted, and the bone chips were removed from the receiver bottle with a sampler spoon. Using a Petri dish and forceps, bone samples then were separated out from large blood clot pieces and tissues. The bone then was packed into a 50 ml conical tube, and the total volume was recorded. The total volume of bone chips was split by separating half for collagenase treatment and half for fresh chips. The chips designated for collagenase treatment were placed into a sterile 500 ml receiver bottle, and the fresh chips were placed into a 500 ml receiver bottle and covered with 0.9% saline and ACD-A at a volume ratio of 9 parts saline to one part ACD-A.

A collagenase solution then was prepared by mixing a collagenase powder with 1× Phosphate Buffered Saline ("PBS") in an amount of 1 mg collagenase for each milliliter of PBS. The collagenase solution was added to the milled bone designated for the collagenase treatment in an amount of 2 ml collagenase solution for each cc of bone to be treated. The bottle containing the milled bone and the collagenase solution then was placed, with the lid loose, onto a rocker inside a 37° C. incubator for 10 minutes±1 minute. The bottle then was removed from the incubator, and the collagenase solution was decanted into a bottles. The collagenase treated milled bone then was rinsed by adding the same volume of PBS and ACD-A at a volume ratio of 9 parts PBS to one part ACD-A. This rinsing solution then was decanted into the bottle containing the collagenase solution. The rinsing then was repeated, the rinsing solution again was decanted, and the collagenased bone sample was added to the bottle of fresh bone sample. The resulting combined (collagenase treated plus fresh) bone sample then was poured through a 1 mm sieve and placed in a clean bottle. The combined bone sample then was rinsed with Dulbecco's Minimal Essential Medium (DMEM), low glucose, with phenol, prior to antibiotic treatment. A demineralized bone sample also was rinsed with DMEM prior to antibiotic treatment.

A 1× antibiotic solution then was prepared. For each 1 ml of solution, 0.9 ml of DMEM was mixed with 0.005 ml of 10 mg/ml gentamicin sulfate, 0.05 ml of 50 mg/ml vancomycin HCl, and 0.01 ml of 250 µg/ml amphotericin B. Thus, the antibiotic solution included gentamicin sulfate at a concentration of 50 µg/ml, vancomycin HCl at a concentration of 50 µg/ml, and amphotericin B at a concentration of 2.5 µg/ml.

The antibiotic solution then was added to each of the combined bone sample and the demineralized bone sample in an amount of 2 ml for each 1 cc of bone sample. The bottles then were placed onto a rocker inside of a 37° C. incubator, with the lids loose, for no less than 18 hours. The bottles then were removed from the incubator, placed under a biological safety container, and the antibiotic solutions were decanted from each of the combined bone sample, and the demineralized bone sample, and each of the bone samples then was washed with the same volume of PBS. The samples then were shaken vigorously. The rinse solutions from the PBS wash were retained, and the pH of each solution was determined. The samples were washed with PBS until the pH of the rinse solutions was in the range of 5.0 to 7.5. After the PBS washing was completed, PBS was decanted from each of the bone samples, and the same volume of Plasma Lyte-A (Baxter) solution, which includes 140 meq/l Na+, 5 meq/l K+, 98 meq Cl—, 3 meq $Mg^{2+}$, and 27 meq/l acetate, was added to each bone sample. The bone samples were shaken vigorously, and the Plasma Lyte-A washing was repeated twice for each sample.

Using a sampler spoon, a 50 ml conical tube was packed gently with the combined (collagenased and fresh) bone sample, and a demineralized bone sample was packed gently into a 15 ml conical tube. 5 ml of a cryopreservation solution was added to the 15 ml conical tube and shaken vigorously. Each ml of cryopreservation solution included 0.7 ml of 1× Plasma Lyte-A, 0.2 ml of 25% human serum albumin, and 0.1 ml of 1× dimethylsulfoxide (DMSO) (CryoServ.) The final concentration of human serum albumin, therefore, was 5% and the final concentration of dimethylsulfoxide was 10%. After shaking, the demineralized bone sample was transferred to the 50 ml conical tube holding the cancellous bone, and then 10 ml of cryopreservation solution were added to the 50 ml conical tube and shaken vigorously. The entire sample then was placed in a product dose jar. 5 ml of cryopreservation solution then were added to the product dose jar. If the bone product were not covered with solution, up to 5 ml more of cryopreservation solution were added. The jar then was sealed. After the jar was sealed, the product dose jar was placed into a packaging bag. The bag then was sealed. The secondary packaging bag and a package insert then were placed into a tertiary mailer package, which then was heat sealed. The mailer package then was placed into an −80° C. quarantine freezer until the bone product was ready to be used.

Example 2

A bone product from a single donor was prepared as described in Example 1, except that, instead of storing 50 ml samples at −80° C., fourteen 5 cc doses were labeled and stored at −50° C.±5° C. and six 5 cc doses were labeled and stored at −80° C.±5° C. Seventeen days after freezing, three of the doses stored at −50° C. and three of the doses stored at −80° C. were thawed.

The jars containing the frozen bone samples placed in a 37° C. water bath until the entire frozen products were thawed. The jars were removed from the water bath immediately upon thawing, and sprayed with 70% isopropanol. The outsides of the jars then were dried. The jars then were transferred to a biological safety cabinet, the lids were removed, and the thawed cryopreservation solutions were aspirated directly from the jars. 25 ml of Dulbecco's Minimal Essential Medium-low glucose (DMEM-lg) then were added to each of the jars, and the containers were swirled such that the DMEM-lg covered the entire bone samples completely. The DMEM-lg then was aspirated from each jar, and the entire bone samples were transferred to 50 ml conical tubes. An additional 25 ml of DMEM-lg then were added to each of the conical tubes containing the bone samples.

A 1 mg/ml collagenase solution (1 mg/1 ml PBS) was prepared in a 250 ml receiver bottle. 2 ml of collagenase solution were prepared per 1 cc of bone sample.

The DMEM-lg was aspirated from the 50 ml conical tubes containing the bone samples, and then 25 ml of PBS were added to each of the conical tubes, and the tubes were swirled to wash away any remaining DMEM-lg. The washing with PBS was repeated as necessary to remove any DMEM-lg still visible in the bone samples.

After the final PBS wash, the PBS was aspirated off and the bone samples were transferred to 250 ml receiver bottles containing the collagenase solutions. The bottles then were placed onto a rocker inside a 37° C. incubator for 15 minutes±1 minute. The bottles then were removed from the incubator, and the collagenase solutions were pipetted over 70 μm cell strainers into 250 ml conical tubes. The collagenased bone samples then were rinsed with PBS at volumes equal to the original collagenase treatments. The PBS rinses were pipetted over the 70 μm cell strainers into the 250 ml conical tubes. The PBS rinsing was repeated twice, and the conical tubes were placed in a centrifuge (Beckman #GS-6R) and spun at 1960 rpm for 8 minutes (at approximately 878 g). The conical tubes then were transferred to the biological safety cabinet, and the supernatants were aspirated. The pellets then were loosened gently by dragging the tubes across the tube racks. The pellets then were resuspended in appropriate volumes (1 to 4 ml) of PBS/ACD-A (containing 59 ml ACD-A per 500 ml PBS).

Three of the samples that were frozen at −50° C. and three of the samples that were frozen at −80° C. then were tested for cell viability.

Using a 2-20 μl Pipetman pipette (Gilson, No. P20), 20 μl aliquots of the resulting cell suspensions were added to a microcentrifuge tube. 20 μl aliquots of 0.4% Trypan Blue then were added to each of the microcentrifuge tubes, and the contents were mixed by finger tapping. 10 μl of the cell suspensions then were transferred into each side of hemacytometers (Hausser Scientific, Model No. Steri-Cult 200) with a cover slip in place. The cells then were allowed to settle in the counting chambers before starting counts of viable and non-viable cells. The cells were not exposed to the Trypan Blue for more than 10 minutes, to prevent viable cells from absorbing the dye.

With the 10× objective of the microscope, the grid lines on each of the chambers' center 1 mm×1 mm squares were focused. The slides were positioned such that the central areas of the grids were seen. The objective of the microscope then was changed to the 20× objective. The microscope then was focused, and viable and non-viable cells were counted. Viable and non-viable cells in two chambers for each cell suspension were counted. Viable and non-viable cell counts then were determined, from which were calculated the concentration of viable cells, the concentration of all cells, and the % viability of the cells.

In order to be acceptable for in vivo administration, the samples must have a viability of at least 70%, and have a cell density of at least $1 \times 10^3$ cells/cc.

The viability results for each of the samples are given in Table 1 below.

TABLE 1

| Storage temperature | % Viability | Cells/cc |
|---|---|---|
| 50 ± 5° C. | 78.6 | 8.80 × 10$^5$ |
| 50 ± 5° C. | 77.8 | 7.00 × 10$^5$ |
| 50 ± 5° C. | 79.3 | 5.84 × 10$^5$ |
| 80 ± 5° C. | 76.1 | S.60 × 10$^5$ |
| 80 ± 5° C. | 77.0 | S.36 × 10$^5$ |
| 80 ± 5° C. | 81.1 | 6.16 × 10$^5$ |

The above data shows that acceptable viability data were obtained for each sample tested, and that cancellous bone prepared in accordance with the present invention can be stored at −80° C.±5° C. at least for seventeen days.

With respect to some applications, surgeons may need to store the cancellous bone at temperature higher than −80° C., such as −50° C. The above data shows that the cancellous bone may be stored at −50° C. and still retain acceptable viability.

Example 3

23 samples of collagenase-treated bone were prepared as described in Example 1, except that the bone samples were treated with collagenase at concentrations from 0.167 mg/ml to 3 mg/ml as given in Table 2 below, and for a period of time from 5 min. to 24 hrs., also given in Table 2 below, and the bone samples were not frozen. The volume of each bone sample and the total volume of collagenase used to treat each bone sample also are given in Table 2 below.

The fresh bone samples were tested for % viability and cell density as described in Example 2. The results are given in Table 2 below.

TABLE 2

| Sample | Donor | Carrier for Collagenase | Conc. | Duration | Volume of Bone (cc) | Volume of Collagenase (ml) | Viability | Cell Yield | Cells/cc Bone |
|---|---|---|---|---|---|---|---|---|---|
| 1 | 020505 | DMEM | 0.5 mg/ml | 24 hrs | 18 | 50 | 91.0% | 6.12E+06 | 3.40E+05 |
| 2 | 020805 | DMEM | 0.5 mg/ml | 24 hrs | 12.5 | 30 | 83.5% | 1.68E+05 | 1.34E+04 |
| 3 | 121404 | DMEM | 0.5 mg/ml | 3 hrs | 5 | 30 | 84.0% | 4.80E+05 | 9.60E+04 |
| 4 | 121404 | DMEM | 1.5 mg/ml | 3 hrs | 10 | 30 | 81.0% | 4.40E+06 | 4.40E+05 |
| 5 | 012105 | DMEM | 3 mg/ml | 3 hrs | 10 | 30 | 86.0% | 6.24E+06 | 6.24E+05 |
| 6 | 020805 | DMEM | 3 mg/ml | 3 hrs | 12.5 | 30 | 91.0% | 1.62E+06 | 1.30E+05 |
| 7 | 011305 | DMEM | 3 mg/ml | 3 hrs | 10 | 30 | 86.0% | 1.53E+05 | 1.53E+04 |
| 8 | 020505 | DMEM | 3 mg/ml | 3 hrs | 10 | 50 | 77.6% | 9.35E+06 | 9.35E+05 |
| 9 | 121804 | DMEM | 0.167 mg/ml | 3 hrs | 20 | 60 | 74.0% | 4.77E+05 | 2.39E+04 |
| 10 | 121804 | DMEM | 0.833 mg/ml | 3 hrs | 20 | 60 | 78.0% | 2.65E+06 | 1.33E+05 |
| 11 | B-031505 | DMEM | 3 mg/ml | 1 hr | 20 | 60 | n/a | 1.00E+06 | 5.00E+04 |
| 12 | 022405 | DMEM | 3 mg/ml | 3 hrs | 25 | 50 | 76.0% | 1.20E+05 | 4.80E+03 |
| 13 | 030905 | DMEM | 3 mg/ml | 3 hrs | 20 | 50 | 94.0% | 1.40E+07 | 6.99E+05 |
| 14 | 022405 | DMEM | 3 mg/ml | 3 hrs | 10 | 25 | 94.7% | 3.63E+05 | 3.63E+04 |
| 15 | 030905 | DMEM | 3 mg/ml | 24 hrs | 10 | 30 | 92.8% | 3.59E+06 | 3.59E+05 |
| 16 | 040705 | Saline | 3 mg/ml | 15 min | 10 | 30 | 66.0% | 1.30E+05 | 1.30E+04 |
| 17 | 040705 | PBS | 3 mg/ml | 10 min | 5 | 30 | 90.4% | 2.08E+05 | 4.16E+04 |
| 18 | 040705 | PBS | 3 mg/ml | 20 min | 10 | 25 | 83.0% | 1.83E+06 | 1.83E+05 |
| 19 | 040705 | PBS | 3 mg/ml | 30 min | 10 | 30 | 95.0% | 3.58E+06 | 3.58E+05 |
| 20 | 041305 | PBS | 3 mg/ml | 5 min | 15 | 30 | 92.1% | 2.05E+06 | 1.37E+05 |
| 21 | 041305 | PBS | 3 mg/ml | 10 min | 15 | 30 | 96.2% | 1.64E+06 | 1.09E+05 |
| 22 | 041305 | PBS | 3 mg/ml | 30 min | 15 | 30 | 91.9% | 3.83E+06 | 2.55E+05 |
| 23 | 041305 | PBS | 3 mg/ml | 1 hr | 15 | 30 | 90.9% | 1.78E+07 | 1.18E+06 |

The above data shows that cancellous bone treated with collagenase at various concentrations and for various periods of time in accordance with the present invention retain acceptable viability.

Example 4

In this example, two samples of cells obtained from cancellous bone samples treated with collagenase are tested for their ability to differentiate into osteogenic cells.

A stock of a standard culture medium was prepared by pipetting 111 ml of FBS and 11 ml of antibiotic-antimycotic (Invitrogen Cat. No. 15240-062) into 1,000 ml of DMEM-Ig to provide a medium having a final concentration of 10% FBS and 1% antibiotic-antimycotic.

A stock of a culture medium including osteogenic supplements (OS medium) was prepared by mixing 246 ml of the standard medium with 25 μl of 1 mM dexamethasone solution, 2.5 ml of 1M β-glycerophosphate (βGP) solution, and 1.25 ml of 10 mM ascorbic acid-2-phosphate (AsAP) solution in a 500 ml sterile bottle. The materials are mixed by swirling the bottle gently for 30 seconds. The medium then is poured into the reservoir of a 500 ml 0.2μ filter with storage system. A vacuum line then is attached to the 500 ml 0.2μ filter, and the medium is filter sterilized. The reservoir then is removed and replaced with a cap. The OS medium is stored at 2° to 8° C.

A Fast Violet B solution was prepared by placing a Sigma® Fast Violet B Salt Capsule into 48 ml of distilled water. The resulting solution then was aliquoted into two 50 ml conical tubes with 12 ml of solution being added to each tube. The tubes then were stored at 4° C.

A citrate solution was prepared by diluting 2 ml of Sigma® Citrate Concentrated Solution to 100 ml with distilled water. The citrate solution was stored at 4° C.

Two collagenase-treated cancellous bone samples were prepared as described in Example 1, and collagenase released (CR) cells from such samples were obtained as described in Example 2.

CR cells were plated at a density of 0.5-5.0×10⁶ cells per well in a 6-well plate using 3 ml of the standard medium hereinabove described. The plate was labeled "PO", and covered with a lid, and transferred to a 37° C. incubator set at 5% CO₂ and 90%±5% humidity. Medium changes were performed twice weekly with a medium volume of 3 ml per well.

Starting on day 7, the plate was examined for cell growth. Confluent cultures were trypsinized for cells between day 14 and day 21.

An appropriate volume of trypsin was warmed to 20° C.-37° C. in a water bath. The plate that is to be trypsinized was removed from the incubator. The medium was aspirated off, and 1.5 ml of trypsin was added to each well to be trypsinized. The plate was placed back in the 37° C. incubator for 5 minutes. The plate then was removed from the incubator, and the sides and bottom of the plate were tapped to dislodge attached cells. 3 ml of standard medium then was added to the wells, the cell suspensions then were mixed, and the entire volumes from the wells were transferred into a 5.0 ml conical tube. The wells then were rinsed with 3 ml of standard medium, and the rinse medium was added to the tube. The total volume of the tube then was brought to 45 ml.

The tube then was placed in a centrifuge, and spun at 1,960 rpm for 8 minutes (about 878 g). The supernatant then was aspirated off, and the pellet was loosened gently by dragging the tube across a tube rack. The pellet then was resuspended in an appropriate volume of standard medium (about 1 to about 3 ml) for cell counting.

A 20 μl aliquot of the cell suspension then was tested for % viability and cell density as described in Example 2.

The cells then were plated at a density of 30×10³ cells (±15×10³ cells) per well in a 6-well plate using 3 ml standard medium. The plate then was labeled "OS", covered with a lid, and transferred to a 37° C. incubator set at 5% CO₂ and 90%±5% humidity. The plate was incubated for 24 to 48 hours.

The OS medium was warmed to 20°-37° C. in a water bath. The standard medium then was aspirated off from each well of the plate, and 3 ml of OS medium then was added to each well. The OS medium was changed every third or fourth day, and the cultures were assayed for alkaline phosphatase expression between days 7 and 14.

Alkaline phosphatase staining then was conducted. Each well was rinsed twice with 1 ml of PBS. A fixative solution then was prepared by mixing two volumes of citrate working solution with three volumes of acetone. Each well then was fixed for one minute with 1 ml of the fixative solution.

0.5 ml of Sigma® alkaline solution naphthol AS-MX phosphate was added to 12 ml of Fast Violet B solution. The solution then was covered with aluminum foil to protect it from light. 1 ml of the Fast Violet B/naphthol solution then was added to each well.

The plate then was incubated at room temperature, in the dark for one hour. The wells then were aspirated, and rinsed twice with 1 ml of distilled water. Cell cultures that exhibited a distinct pink stain in some or all of the cells were positive. Cell cultures from both samples of cells gave positive results.

Example 5

Cancellous bone, which included cancellous bone treated with collagenase and cancellous bone that was untreated, was prepared as described in Example 1. The cortical bone was processed, milled, and washed according to normal standard operating procedure for tissue products. The cortical bone then was sieved through a 1,500µ sieve stacked atop a 780µ sieve stacked atop a 125µ sieve stacked onto a receiving pan with WFI (water for injection) quality water. Larger fragments, herein referred to as cortical bone chips, which were above the 780µ sieve and below the 1,500µ sieve were transferred to 50 mL conical tubes. Smaller fragments, herein referred to as cortical bone powder, which were above the 125µ sieve and below the 780µ sieve, were transferred to another set of 50 ml conical tubes. After sieving, the cortical bone samples were processed separately using the same methods described below. The samples are referred to hereinbelow as cortical bone samples.

Cortical bone samples were treated with 0.5M hydrochloric acid for 70 minutes, at a ratio of 1 cc of cortical bone fragments to 17 cc of 0.5M hydrochloric acid (HCl) at 4° C. in roller bottles under constant rolling. The HCl was decanted off each sample and the samples were neutralized with a 5% Sodium Phosphate/PBS solution. The sample was shaken vigorously, and the 5% Sodium Phosphate/PBS solution was decanted off. The sample was then rinsed with 1×PBS, shaken vigorously, and the pH of the PBS was taken. If the pH of the PBS were outside a 5-7.5 pH range, the sample was rewashed with 1×PBS until the pH was between 5 and 7.5 pH range, the sample was rewashed with 1×PBS until the pH was between 5 and 7.5 pH. The bone sample then was rinsed through a 125 µM sieve and placed into a clean bottle. The sample was then treated with a 1× antibiotic solution consisting of 0.9 ml of DMEM mixed with 0.005 ml of 10 mg/ml gentamicin sulfate, 0.05 ml of 50 mg/ml vancomycin HCl, and 0.1 ml of 250 µg/ml amphotericin B resulting in a final antibiotic solution of gentamycin sulfate (50 µg/ml), vancomycin HCl (50 µg/ml) and amphotericin B (2.5 µg/ml). The bottles then were capped with a gas permeable lid and transferred into a 37° C. incubator for 18+ hours. The bottles then were removed from the incubator, placed into a BSC (biological safety cabinet), and the antibiotic solution was decanted off. The bone samples were then washed with the same volume of PBS, shaken vigorously, and the PBS decanted off. The bone samples then were washed three times in the same fashion with Plasmalyte-A. After washing, the bone samples were transferred to 50 ml conical tubes using sampler spoons.

Using a sampler spoon and tweezers, 7 cc cancellous bone, 3 cc of cortical chips, and 2 cc of cortical powder processed as described above were added to a product dose jar. Cryopreservation solution, consisting of 1× Plasmalyte-A, 0.2 mL of 25% human serum albumin, and 0.1 ml of 1× dimethylsulfoxide (DMSO) (CryoServ) per m L, then was added to cover the material within the jar. The jar then was sealed tightly and shaken vigorously. After the jar was sealed, the product dose jar was placed into a packaging bag and the bag was then sealed. The secondary packaging bag then was placed into a storage containing and placed into an −80° C. quarantine freezer until the product was used for further study.

Example 6

Five lots of "test" bone samples, prepared as described in Example 5, and five lots of "control" bone samples, prepared as described in Example 1, were obtained from five donors. From each donor, a test bone sample and a control bone sample was prepared.

Prior to implantation, the bone samples were thawed either at room temperature, or in a water bath at a temperature no greater than 39° C. Once the bone samples were thawed completely, as much cryoprotectant was decanted off and discarded. Sterile saline then was added to the jars to cover the bone samples. The bone samples were implanted within 4 hours of being thawed. The samples then were removed from the sterile saline, weighed, and were placed gently in sterile syringes.

25 athymic male nude rats, each weighing at least 100 grams at the beginning of the study, were divided into five groups of 5 rats each. Each rat of each group received a test bone sample and a control bone sample from the same donor.

Each rat was given one pre-operative injection of buprenorphine (0.1 mg/kg IP), and then anesthetized with inhalant isoflurane gas. The upper portion of the back then was clipped and scrubbed for surgery. Hemostasis was employed as necessary. Doses of anesthesia were given as needed to maintain the proper plane of unconsciousness.

Incisions of approximately 1 cm were made in the skin over each scapula. Pockets were made in the subcutaneous tissue by blunt and sharp dissection. Approximately 300±25 mg of either the test bone sample or the control bone sample were placed into each pocket. The subcutaneous tissue and skin then were closed with sutures. After the rats recovered from the anesthesia, they were returned to their cages. The rats received one post-operative injection of buprenorphine (0.1 mg/kg IP) for analgesia on the day after surgery.

The rats were weighed and then euthanized on Day 28 with $CO_2$. The implant sites then were opened and observed in order to confirm the retention of the implanted bone samples. The bone samples with adjacent soft tissue were excised, fixed, and processed for pathology.

Gross necropsy findings, and most critically, the microscopic analyses were the main study endpoints determining the presence or absence of osteoinduction at the implant sites.

Evaluation of osteoinduction was based on the successful implantation of all bone samples and the survival of sufficient animals until the study endpoint. Also, at recovery of the implants, the implant sites must grossly be free from bacterial contamination as evidenced by the absence of exudates, inflammation, or frank tissue destruction (necrosis). Sites that were associated with local infection that resolved during the course of the study were considered suspect. Microscopic evidence of the bone sample must be present at the implant site.

The bone samples and the surrounding tissue were fixed in 10% neutral buffered formalin (NBF) prior to routine histology, decalcification, and processing. The samples then were processed into paraffin, and sections from 3 to 6 microns thick were cut and mounted onto glass slides and stained with hematoxylin and eosin. Blocks were faced as necessary. Sections were taken from at least three levels within the block. The slides were evaluated for evidence of osteoinduction. More particularly, the slides were evaluated for the presence of the following:
1. chondroblasts;
2. chondroytes;
3. osteoblasts;
4. osteocytes;
5. cartilage;
6. osteoid tissue;
7. new bone; and,
8. new bone marrow.

Evidence of osteoinduction was graded as follows:
0—no evidence of new bone formation
1—1-25% of field shows evidence of new bone formation
2—26-50% of field shows evidence of new bone formation
3—51-75% of field shows evidence of new bone formation
4—76-100% of field shows evidence of new bone formation Samples having a score of 0 were considered non-osteoinductive while samples having a score of from 1 to 4 were considered osteoinductive.

The results for the test and control samples from each donor for each rat are given in Table 3 below. As shown in Table 3, an "X" indicates the presence of the element, while a minus sign "−", indicates that the element was not present.

TABLE 3

TEST ARTICLE-DONOR 1
OBSERVED ELEMENTS OF NEW BONE FORMATION

| Rat Number | Site L OR R | CHONDROBLASTS/ CYTES | OSTEOBLASTS/ CYTES | CARTILAGE/ OSTEOID | NEW BONE | BONE MARROW | ORIGINAL DBM | GRADE (0-4) |
|---|---|---|---|---|---|---|---|---|
| 1 | R | — | X | — | X | X | X | 1 |
| 2 |   | — | — | — | — | — | X | 0 |
| 3 |   | — | — | — | — | — | X | 0 |
| 4 |   | — | — | — | — | — | X | 0 |
| 5 |   | — | X | — | X | — | X | 1 |

TEST ARTICLE-DONOR 2
OBSERVED ELEMENTS OF NEW BONE FORMATION

| Rat Number | Site L OR R | CHONDROBLASTS/ CYTES | OSTEOBLASTS/ CYTES | CARTILAGE/ OSTEOID | NEW BONE | BONE MARROW | ORIGINAL DBM | GRADE (0-4) |
|---|---|---|---|---|---|---|---|---|
| 1 | R | — | X | — | X | — | X | 1 |
| 2 |   | X | X | X | X | X | X | 1 |
| 3 |   | X | X | X | X | X | X | 1 |
| 4 |   | X | X | X | X | — | X | 1 |
| 5 |   | — | X | — | X | X | X | 1 |

TEST ARTICLE-DONOR 3
OBSERVED ELEMENTS OF NEW BONE FORMATION

| Rat Number | Site L OR R | CHONDROBLASTS/ CYTES | OSTEOBLASTS/ CYTES | CARTILAGE/ OSTEOID | NEW BONE | BONE MARROW | ORIGINAL DBM | GRADE (0-4) |
|---|---|---|---|---|---|---|---|---|
| 1 | R | — | — | — | — | — | X | 0 |
| 2 |   | — | — | — | — | — | X* | 0 |
| 3 |   | X | X | X | X | X | X | 4 |
| 4 |   | X | X | X | X | X | X | 1 |
| 5 |   | — | — | — | — | — | X | 0 |

TEST ARTICLE-DONOR 4
OBSERVED ELEMENTS OF NEW BONE FORMATION

| Rat Number | Site L OR R | CHONDROBLASTS/ CYTES | OSTEOBLASTS/ CYTES | CARTILAGE/ OSTEOID | NEW BONE | BONE MARROW | ORIGINAL DBM | GRADE (0-4) |
|---|---|---|---|---|---|---|---|---|
| 1 | R | X | X | — | X | — | X | 1 |
| 2 |   | — | — | — | — | — | X | 0 |
| 3 |   | X | — | X | — | — | X | 1 |
| 4 |   | — | — | — | — | — | X | 0 |
| 5 |   | X | X | X | X | X | X | 1 |

TEST ARTICLE-DONOR 5
OBSERVED ELEMENTS OF NEW BONE FORMATION

| Rat Number | Site L OR R | CHONDROBLASTS/ CYTES | OSTEOBLASTS/ CYTES | CARTILAGE/ OSTEOID | NEW BONE | BONE MARROW | ORIGINAL DBM | GRADE (0-4) |
|---|---|---|---|---|---|---|---|---|
| 1 | R | — | — | — | — | — | X | 0 |
| 2 |   | X | X | X | X | X | X | 1 |
| 3 |   | — | X | — | X | — | X | 1 |

TABLE 3-continued

| | | | | | | | |
|---|---|---|---|---|---|---|---|
| 4 | | X | X | X | X | X | X | 1 |
| 5 | | — | — | — | — | — | X | 0 |

CONTROL ARTICLE-DONOR 1
OBSERVED ELEMENTS OF NEW BONE FORMATION

| Rat Number | Site L OR R | CHONDROBLASTS/ CYTES | OSTEOBLASTS/ CYTES | CARTILAGE/ OSTEOID | NEW BONE | BONE MARROW | ORIGINAL DBM | GRADE (0-4) |
|---|---|---|---|---|---|---|---|---|
| 1 | L | — | — | — | — | — | X | 0 |
| 2 | | — | — | — | — | — | X | 0 |
| 3 | | — | — | — | — | — | X | 0 |
| 4 | | — | — | — | — | — | X | 0 |
| 5 | | — | — | — | — | — | X | 0 |

CONTROL ARTICLE-DONOR 2
OBSERVED ELEMENTS OF NEW BONE FORMATION

| Rat Number | Site L OR R | CHONDROBLASTS/ CYTES | OSTEOBLASTS/ CYTES | CARTILAGE/ OSTEOID | NEW BONE | BONE MARROW | ORIGINAL DBM | GRADE (0-4) |
|---|---|---|---|---|---|---|---|---|
| 1 | L | — | X | — | X | — | X | 1 |
| 2 | | — | X | — | X | X | X | 1 |
| 3 | | X | X | — | X | X | X | 1 |
| 4 | | — | X | X | X | X | X | 1 |
| 5 | | — | — | — | — | — | X | 0 |

CONTROL ARTICLE-DONOR 3
OBSERVED ELEMENTS OF NEW BONE FORMATION

| Rat Number | Site L OR R | CHONDROBLASTS/ CYTES | OSTEOBLASTS/ CYTES | CARTILAGE/ OSTEOID | NEW BONE | BONE MARROW | ORIGINAL DBM | GRADE (0-4) |
|---|---|---|---|---|---|---|---|---|
| 1 | L | — | — | — | — | — | X | 0 |
| 2 | | — | — | — | — | — | X | 0 |
| 3 | | — | — | — | — | — | X | 0 |
| 4 | | — | — | — | — | — | X | 0 |
| 5 | | — | — | — | — | — | X | 0 |

CONTROL ARTICLE-DONOR 4
OBSERVED ELEMENTS OF NEW BONE FORMATION

| Rat Number | Site L OR R | CHONDROBLASTS/ CYTES | OSTEOBLASTS/ CYTES | CARTILAGE/ OSTEOID | NEW BONE | BONE MARROW | ORIGINAL DBM | GRADE (0-4) |
|---|---|---|---|---|---|---|---|---|
| 1 | L | — | X | — | X | X | X | 1 |
| 2 | | — | — | — | — | — | X | 0 |
| 3 | | — | X | — | X | X | X | 1 |
| 4 | | — | — | — | — | — | X | 0 |
| 5 | | — | — | — | — | — | X | 0 |

CONTROL ARTICLE-DONOR 5
OBSERVED ELEMENTS OF NEW BONE FORMATION

| Rat Number | Site L OR R | CHONDROBLASTS/ CYTES | OSTEOBLASTS/ CYTES | CARTILAGE/ OSTEOID | NEW BONE | BONE MARROW | ORIGINAL DBM | GRADE (0-4) |
|---|---|---|---|---|---|---|---|---|
| 1 | L | — | X | — | X | — | X | 1 |
| 2 | | — | — | — | — | — | X | 0 |
| 3 | | — | — | — | — | — | X | 0 |
| 4 | | — | — | — | — | — | X | 0 |
| 5 | | — | — | — | — | — | X | 0 |

The results for each of the test and control articles are summarized as follows:

Test Article from Donor 1—Evidence of osteoinduction, including osteoblasts/osteocytes, and new bone, was found in two of the implants. Bone marrow also was found in one of the implants. Thus, the test article from Donor 1 was considered to be osteoinductive.

Test Article from Donor 2—Evidence of osteoinduction, including osteoblasts/osteocytes and new bone, was found in all five of the implants. Chondroblasts/chondrocytes, cartilage/osteoid tissue, and bone marrow were found in three of the implants. Thus, the test article from Donor 2 was considered to be osteoinductive.

Test Article from Donor 3—Evidence of osteoinduction, including chondroblasts/chondrocytes, osteoblasts/osteocytes, cartilage/osteoid tissue, new bone, and bone marrow, was found in two of the implants. Thus, the test article from Donor 3 was considered to be osteoinductive.

Test Article from Donor 4—Evidence of osteoinduction, including chondroblasts/chondrocytes, was found in three of the implants. Osteoblasts/osteocytes, cartilage/osteoid tissue, and new bone were found in two of the implants. Bone marrow was found in one of the implants. Thus, the test article from Donor 4 was considered to be osteoinductive.

Test Article from Donor 5—Evidence of osteoinduction, including osteoblasts/osteocytes, was found in three of the implants. Chondroblasts/chondrocytes, cartilage/osteoid tissue, and bone marrow were found in two of the implants. Thus, the test article from Donor 5 was considered to be osteoinductive.

With respect to the control articles, no evidence of osteoinduction was found in any of the implant sites from the control articles from Donor 1 and Donor 3. Thus, the control articles from Donor 1 and Donor 3 were considered to be non-osteoinductive.

The results with respect to the remaining control articles were as follows:

Control Article from Donor 2—Evidence of osteoinduction, including osteoblasts/osteocytes and new bone, was found in four of the implants. Bone marrow was found in three of the implants, and chondroblasts/chondrocytes and cartilage/osteoid tissue were found in one of the implant sites. Thus, the control article from Donor 2 was considered to be osteoinductive.

Control Article from Donor 4—Evidence of osteoinduction, including osteoblasts/osteocytes, new bone, and bone marrow, was found in two of the implant sites. Thus, the control article from Donor 4 was considered to be osteoinductive.

Control Article from Donor 5—Evidence of osteoinduction, including osteoblasts/osteocytes and new bone, was found in one of the implant sites. Thus, the control article from Donor 5 was considered to be osteoinductive.

Example 7

The test and control samples from Donors 1 through 5 as described in Example 6 hereinabove were tested for cell density and cell viability as described in Example 2 hereinabove. The cell density results are given in Table 4 below, and the cell viability results are given in Table 5 below.

TABLE 4

| | Cell Density (cells/cc) | | |
|---|---|---|---|
| Donor | Control Sample | Test Sample | Difference |
| 1 | $7.07 \times 10^6$ | $4.38 \times 10^6$ | $-2.69 \times 10^6$ |
| 2 | $1.43 \times 10^6$ | $2.48 \times 10^6$ | $1.05 \times 10^6$ |
| 3 | $4.07 \times 10^6$ | $3.16 \times 10^6$ | $-0.93 \times 10^6$ |
| 4 | $2.47 \times 10^6$ | $2.24 \times 10^6$ | $-0.23 \times 10^6$ |
| 5 | $1.23 \times 10^6$ | $4.05 \times 10^6$ | $2.82 \times 10^6$ |

TABLE 5

| | Cell Viability | | |
|---|---|---|---|
| Donor | Control Sample | Test Sample | Difference |
| 1 | 90.2% | 82.0% | −8.2% |
| 2 | 80.6% | 68.6% | −12.0% |
| 3 | 86.1% | 80.5% | −5.6% |
| 4 | 88.3% | 79.6% | −8.7% |
| 5 | 82.4% | 79.9% | −2.5% |

Example 8

The control and test samples from each of Donors 1 through 5 were tested for osteodifferentiation in a revision of the method described in Example 4 hereinabove. In this example, two bone samples from each of the control and test samples from Donors 1 through 5 of cells were obtained from cancellous bone samples treated with collagenase are tested for their ability to differentiate into osteogenic cells.

A stock of a standard culture medium was prepared by pipetting 111 ml of FBS and 11 ml of antibiotic-antimycotic (Invitrogen Cat. No. 15240-062) into 1,000 ml of DMEM-low glucose (DMEM-Ig) to provide a medium having a final concentration of 10% FBS and 1% antibiotic-antimycotic.

A stock of a culture medium including osteogenic supplements (OS medium) was prepared by mixing 246 ml of the standard medium with 25 µl of 1 mM dexamethasone solution, 2.5 ml of 1M β-glycerophosphate (βGP) solution, and 1.25 ml of 10 mM ascorbic acid-2-phosphate (AsAP) solution in a 500 ml sterile bottle. The materials are mixed by swirling the bottle gently for 30 seconds. The medium then is poured into the reservoir of a 500 ml 0.2µ filter with storage system. A vacuum line then is attached to the 500 ml 0.2µ filter, and the medium is filter sterilized. The reservoir then is removed and replaced with a cap. The OS medium is stored at 2°-8° C.

A BCIP/NBT working solution was prepared by placing 1 drop each of Reagent 1, 2, and 3 from the BCIP/NBT Alkaline Phosphatase Substrate Kit IV into 5 mL of Tris-HCL Buffer 100 mM. The resulting solution then was aliquoted into a 50 ml conical tube and stored at 4° C.

One of the two collagenase-treated cancellous bone samples (Bone Sample 1) was prepared as described in Example 1, and collagenase released (CR) cells from such samples were obtained as described in Example 2. The cryopreservation solution from Bone Sample 1 was placed into a conical tube and set aside. The other bone sample (Bone Sample 2) was thawed in a water bath at 37° C. and then the cryopreservation solution was aspirated off and added to the conical tube containing the cryopreservation solution from Bone Sample 1. 10 mL of standard medium was then added to the Bone Sample 2 container, the sample was shaken, and the medium was transferred to the conical tube containing the cryopreservation solution from Bone Sample 1 and 2. Then the tube was placed in a centrifuge, and spun at 1,960 rpm for 8 minutes (about 878 g). The media was then aspirated from the tube and the cells were resuspended in 4 mL of standard medium and placed into a well in a 6 well plate labeled 'Cells from Cryopreservation Solution (Samples. 1 & 2). The remaining bone chips of Bone Sample 2 were then transferred to another well in the 6 well plate labeled Osteogenic Sample 2 Bone Chips.

CR cells were plated into one well of the six well plate in 4 mL of standard medium hereinabove described. The well was labeled as CR Cells Sample 1. Bone samples were placed into 3 wells of the same 6 well plate at 1.5-2 cc per well with 4 mL of standard media per well and all three wells were labeled as Osteogenic Sample 1. The plate was covered with a lid, and transferred to a 37° C. incubator set at 5% $CO_2$ and 90%±5% humidity. Medium changes were performed every 2-4 days with a medium volume of 4 ml per well.

Plates were examined daily until confluence was greater than 60%. Once confluence was greater than 60%, plates were trypsinized for cells.

An appropriate volume of trypsin was warmed to 37° C. in a water bath. The plate that is to be trypsinized was removed from the incubator. The medium was aspirated off, and each well containing bone chips was washed with 3.5 mL of PBS and the well containing cells with 3 mL. The PBS was then aspirated and 2 mL of trypsin was added to each well containing bone chips and 1.5 mL to each well containing cells. The plate was placed back in the 37° C. incubator for 5 minutes. The plate then was removed from the incubator, and the sides and bottom of the plate were tapped to dislodge attached cells. 3 ml of standard medium then were added to the wells, the cell suspensions then were mixed, and the entire volumes from the wells were transferred into a 50 ml conical tube. The wells then were rinsed with 3 ml of standard medium, and the rinse medium was added to the tube. The total volume of the tube then was brought to 45 ml. The tube then was placed in a centrifuge, and spun at 1,960 rpm for 8 minutes (about 878 g). The supernatant then was aspirated off, and the pellet was loosened gently by dragging the tube across a tube rack. The pellet then was resuspended in 9 mL of standard medium. 3 mL of the cell suspension was plated in each of 3 wells of a 6 well plate and the plate was covered and transferred to a 37 C incubator. The plate then was labeled "OS", covered with a lid, and transferred to a 37° C. incubator for 24 to 48 hours.

The OS medium was warmed to 37° C. in a water bath. The standard medium then was aspirated off from each well of the plate, and 3 ml of OS medium then was added to each well. The OS medium was changed every third or fourth day, and the cultures were assayed for alkaline phosphatase expression between days 7 and 14.

Alkaline phosphatase staining then was conducted. Each well was rinsed twice with 1 ml of PBS. 1 ml of BCIP/NBT Working solution was added to each well and plates were incubated at room temperature in the dark for 6-30 hours. All wells were then evaluated for the presence of the blue/purple color of the positive Alkaine Phosphatase reaction. Each of the test and control samples from each of Donors 1 through 5 was positive for osteodifferentiation.

Example 9

Evaluation of cortical chip size was performed through a series grinding and sifting procedures in which cortical bone was sorted into multiple size ranges. The various sized cortical chip fragments were then compared. Blinded evaluation of mixtures of cancellous chips and cortical chips of various chip sizes with varied cortical to cancellous ratios was performed by seven people with previous experience in osteoimplantation techniques. Six of the seven persons evaluating the trial mixtures selected the same chip size and formulation when asked to select the sample having optimal physical characteristics, such optimal mixture was found to comprise 70% cancellous bone chips, and 30% cortical bone chips of 780 microns to 1500 microns in size, compared to a mixture of 100% cancellous bone chips. Blinded evaluation of this optimal mixture was then performed by orthopedic surgeons, operating under test conditions similar to typical surgical conditions, also found products comprising this optimal mixture to exhibit superior handling and physical characteristics.

The disclosures of all patents, publications (including published patent applications), depository accession numbers, and database accession numbers were incorporated herein by reference to the same extent that each patent, publication, depository accession number and database accession number were specifically and individually incorporated by reference.

It is to be understood, however, that the scope of the present invention is not to be limited to the specific embodiments described above. The invention may be practiced other than as particularly described and still be within the scope of the accompanying claims.

What is claimed is:

1. A bone implant, comprising:
   (i) cancellous bone, wherein said cancellous bone is essentially free of blood cells and is treated with at least one loosening agent for a time and at a concentration to partially but not completely digest the cancellous bone, thereby loosening but retaining osteogenic cells in the cancellous bone, said osteogenic cells in the cancellous bone being viable cells; and
   (ii) bone that is not treated with the at least one loosening agent, wherein the cancellous bone and the bone are combined and stored in a sealed container.

2. The implant of claim 1, wherein said at least one loosening agent is selected from the group consisting of collagenase and digestive enzymes.

3. The implant of claim 2, wherein said at least one loosening agent is collagenase.

4. The implant of claim 3, wherein said bone is treated with said collagenase at a concentration of from about 0.1 mg/ml to about 3 mg/ml.

5. The implant of claim 4, wherein said bone is treated with said collagenase at a concentration of from about 1.0 mg/ml to about 3 mg/ml.

6. The implant of claim 3, wherein said bone is treated with said collagenase for a period of time from about 5 minutes to about 3 hours.

7. The implant of claim 6, wherein said bone is treated with said collagenase for a period of time from about 5 minutes to about minutes.

8. The implant of claim 3, wherein said bone is treated with said collagenase at a concentration of about 1.0 mg/ml for a period of time from about 10 minutes.

9. A bone implant comprising:
   (i) cancellous bone essentially free of blood cells, wherein the cancellous bone is treated with at least one loosening agent for a time and at a concentration to partially but not completely digest the cancellous bone, thereby loosening but still retaining osteogenic cells in the cancellous bone, said osteogenic cells in the cancellous bone being viable cells; and
   (ii) cortical bone which has been treated with at least one demineralization agent for a time and at a concentration to expose osteoinductive proteins present in the cortical bone, wherein the cancellous bone and the cortical bone are combined in a sealed container, and wherein the cortical bone is not treated with the at least one loosening agent.

10. The implant of claim 9, wherein said at least one demineralization agent is hydrochloric acid.

11. The implant of claim 10, wherein said cortical bone is treated with said hydrochloric acid at a concentration of from about 0.1N to about 12N.

12. The implant of claim 11, wherein said cortical bone is treated with said hydrochloric acid at a concentration of about 0.5N.

13. The implant of claim 9, wherein said cortical bone is treated with said at least one demineralization agent for a period of time of from about 1 minute to about 72 hours.

14. The implant of claim 13, wherein said cortical bone is treated with said at least one demineralization agent for a period of time of from about 50 minutes to about 70 minutes.

15. The implant of claim 9, wherein said cortical bone comprises particles having a $D_{90}$ of less than about 1,500 microns.

16. The implant of claim 15, wherein said particles have a $D_{90}$ from about 125 microns to about 1,500 microns.

17. The implant of claim 16, wherein said particles have a $D_{90}$ from about 780 microns to about 1,500 microns.

18. The implant of claim 16, wherein said particles have a $D_{90}$ from about 125 microns to about 780 microns.

19. The implant of claim 15, wherein said cortical bone comprises a first portion comprising particles having a $D_{90}$ of from about 780 microns to about 1,500 microns and a second portion comprising particles having a $D_{90}$ of from about 125 microns to about 780 microns.

20. The bone implant of claim 19, wherein said bone implant includes at least 50 vol. % of said cancellous bone, from about 5 vol. % to about 40 vol. % of said cortical bone particles having a $D_{90}$ of from about 780 microns to about 1,500 microns, and from about 5 vol. % to about 20 vol. % of said cortical bone particles having a $D_{90}$ of from about 125 microns to about 780 microns.

21. The implant of claim 20, wherein said cancellous bone is present in said implant in an amount of from about 55 vol. % to about 85 vol. %.

22. The implant of claim 20, wherein said cortical bone particles having a $D_{90}$ from about 125 microns to about 780 microns are present in an amount of from about 8 vol. % to about 18 vol. %.

\* \* \* \* \*